US00PP12001P2

(12) United States Plant Patent
Kordes

(10) Patent No.: US PP12,001 P2
(45) Date of Patent: Jul. 17, 2001

(54) GRANDIFLORA ROSE PLANT NAMED 'KORBETEILICH'

(75) Inventor: Wilhelm Kordes, Sparrieshoop (DE)

(73) Assignee: Jackson & Perkins Wholesale, Inc., Medford, OH (US)

( * ) Notice: Subject to any disclaimer, the term of this patent is extended or adjusted under 35 U.S.C. 154(b) by 0 days.

(21) Appl. No.: 09/286,131

(22) Filed: Apr. 2, 1999

(51) Int. Cl.[7] ..... A01H 5/00
(52) U.S. Cl. ..... Plt./139
(58) Field of Search ..... Plt./139, 140

*Primary Examiner*—Howard J. Locker
(74) *Attorney, Agent, or Firm*—Klarquist Sparkman Campbell Leigh & Whinston, LLP

(57) ABSTRACT

A grandiflora rose plant having very glossy, dark green, disease resistant foliage; large, bright red flowers of stable color growing singly and in large, open clusters.

1 Drawing Sheet

The present invention relates to a new and distinct variety of rose plant of the grandiflora class which was originated by me by crossing the variety KORbad (not patented) with POULman (U.S. Plant Pat. No. 6,264).

The primary objective of this breeding was to produce a new rose variety having the glossy foliage, upright, bush growth and bright red flowers of the floribunda female parent combined with the large red flowers, vigorous growth and large foliage of the hybrid tea male parent. The objective was substantially achieved, along with other desirable improvements, as evidenced by the following unique combination of characteristics that are outstanding in the new variety and that distinguish it from its parents, as well as from all other varieties of which I am aware:

1. Large, bright flowers;
2. Large, open clusters;
3. Very glossy foliage;
4. Resistance to foliar diseases.

'KORbeteilich' is a vigorous, very disease resistant red grandiflora. Its flower color is very stable through the life of the flower while on the plant or as a garden cut rose. The bright red flower contrasts very well with the very dark green, very glossy foliage. Plants can be grown in U.S.D.A. zones 5–11 without protection. In zones 1–4, winter protection must be provided to insure survival.

Asexual reproduction of this new variety by budding, as performed at Sparrieshoop, Germany and Wasco, Calif. shows that the foregoing and all other characteristics and distinctions come true to form and are established and transmitted through succeeding propagations.

The accompanying illustration shows typical specimens of the vegetative growth and flowers of this new variety in different stages of development, depicted in colors as nearly true as it is reasonably possible to make the same in a color illustration of this character.

The following is a detailed description of my new rose cultivar with color descriptions using terminology in accordance with The Royal Horticultural Society (London) Colour Chart, except where ordinary dictionary significance of color is indicated.

Parentage:

*Seed parent.*—KORbad (not patented).
*Pollen parent.*—POULman (U.S. Plant Pat. No. 6,264).

Classification:

*Botanical.*—*Rosa hybrida.*
*Commercial.*—Grandiflora.

FLOWER

Observations made from specimens grown in a garden environment at Sparrieshoop, Germany and Somis, Calif. from February 1996 to December 1998.

Blooming habit: Continuous.

Bud:

*Size.*—1¾ inches long when the petals start to unfurl.
*Form.*—The bud form is long, pointed ovoid to globular.
*Color.*—When sepals first divide, the bud color is Red Group 44. There is some petal blackening on petal tips and edges under bright, hot conditions. When half blown, the upper sides of the petals are Red Group 44A and the lower sides of the petals are Red Group 44A.
*Sepals.*—Color: Green Group 138B. In bright sun the sepals will acquire a bronze cast that is Greyed-Purple 183B. Surface texture: Covered in fine hairs. There are three lightly appendaged sepals. There are two unappendaged sepals with hairy edges.
*Receptacle.*—Color: Green Group 139C. Shape: Funnel. Size: Medium (7/16" long ×5/16" wide). Surface: Smooth.
*Peduncle.*—Length: Short (averaging 1½ to 2"). Surface: Rough, prickly, glandular. Color: Greyed Red Group 178B. Strength: Stiff, erect.

Bloom:

*Size.*—Large. Average open size is 4".
*Borne.*—Singly and several together in pyramidal shaped, open clusters of three to seven blooms.
*Stems.*—Strength: Strong. Average length is 14–18".
*Form.*—When first open: High centered. Permanence: Retains its form to the end. Outer petals curl back with some quilling.
*Petalage.*—Number of petals under normal conditions: 25–30.
*Color.*—The upper sides of the petals are Red Group 44A. The reverse sides of the petals are Red Group 44A. The base of each petal has on both petal surfaces a small 3/16"×3/16" half moon of Yellow Group 13A color. The major color on the upper side is Red Group 44A.

*Variegations*.—None.

*Discoloration*.—At the end of the first day: No change. At the end of the third day: No change.

*Fragrance*.—Slight.

Petals:

*Texture*.—Thick.

*Shape*.—Round.

*Form*.—Tips slightly recurved. Edges slightly quilled.

*Arrangement*.—Imbricated. Petaloids in the center: Few. Are Red Group 44A, often with a whitish streak. Are of irregular shape between ¼" to ½" long and ⅛" to ¼" wide.

*Persistence*.—Petals drop off cleanly before drying.

*Lastingness*.—On the plant: Long (6–7 days). As a cut flower: Long (7–8 days).

Reproductive parts:

*Anthers*.—Size: Medium. Quantity: Many. Color: Yellow-Orange Group 16B. Arrangement: Regular around styles.

*Filaments*.—Color: Red Group 45D.

*Pollen*.—Color: Yellow-Orange Group 20B.

*Styles*.—Color: Red Group 45B.

*Stigmas*.—Color: Yellow-White Group 158C.

*Hips*.—Produced under hand pollination. Contain 1 to 15 seeds.

Plant:

*Form*.—Bush.

*Growth*.—Vigorous; upright; branching.

*Mature plant*.—Height is 5 to 5½', and width is 3½'.

Foliage: Number of leaflets on normal mid-stem leaves: Five.

*Size*.—Large (6½" long×5" wide).

*Quantity*.—Abundant.

*Color*.—New foliage: Upper and lower surfaces: Greyed-Red Group 178A. Old foliage: Upper Surface: Green Group 139A. Lower Surface: Green Group 139C.

*Shape*.—Pointed oval.

*Texture*.—Upper side: Leathery; glossy.

*Edge*.—Serrated.

*Serration*.—Single; small.

*Petiole rachis*.—Color: Green Group 139D. On the upper surface of the rachis the color is often, especially on newer leaves, Greyed-Red 178A.

*Petiole underside*.—Smooth with occasional prickles.

*Stipules*.—Medium (½"); serrated; bearded.

*Disease resistance*.—Resistant to mildew, blackspot and rust under normal growing conditions.

Wood:

*New wood*.—Color: Greyed-Orange Group 176B. Bark: Smooth.

*Old wood*.—Color: Green Group 137C. When still young but mature, green wood can bronze to almost black. Color is close to Greyed-Purple 187A. Bark: Smooth.

Prickles:

*Quantity*.—On main canes from base: Ordinary. On laterals from main canes: Ordinary.

*Form*.—Medium; straight.

*Color when young*.—Greyed-Orange Group 176A.

*Color when mature*.—Greyed-Orange Group 165D.

Small prickles:

*Quantity*.—On main stalks: None. On laterals: None.

I claim:

1. A new and distinct variety of rose plant of the grandiflora class, substantially as herein shown and described, characterized particularly as to novelty by its very glossy, dark green, disease resistant foliage; large, bright red flowers of stable color growing singly and in large, open clusters.

* * * * *

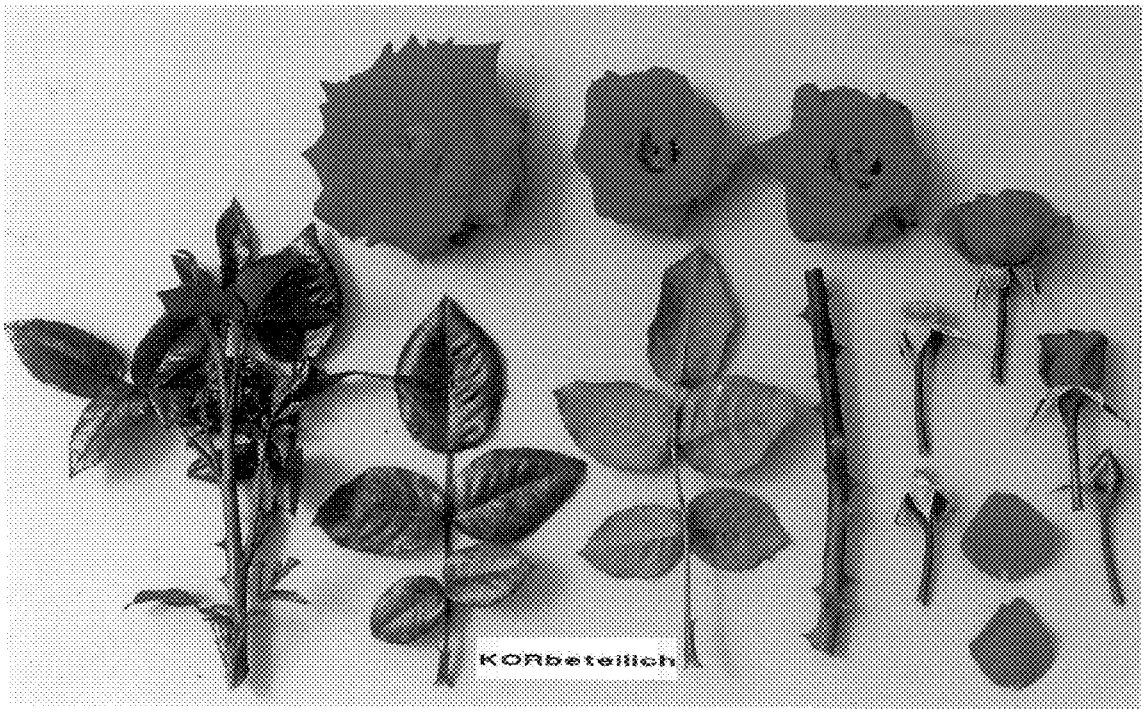
KORbetellich